United States Patent
Eriksson

(10) Patent No.: US 7,997,228 B2
(45) Date of Patent: Aug. 16, 2011

(54) MILK MEASUREMENT AND MILK COLLECTION

(75) Inventor: Jan Eriksson, Uttran (SE)

(73) Assignee: DeLaval Holding AB, Tumba (SE)

( * ) Notice: Subject to any disclaimer, the term of this patent is extended or adjusted under 35 U.S.C. 154(b) by 827 days.

(21) Appl. No.: 10/480,435

(22) PCT Filed: Jun. 7, 2002

(86) PCT No.: PCT/SE02/01104
§ 371 (c)(1),
(2), (4) Date: Dec. 12, 2003

(87) PCT Pub. No.: WO02/100164
PCT Pub. Date: Dec. 19, 2002

(65) Prior Publication Data
US 2004/0154548 A1    Aug. 12, 2004

(30) Foreign Application Priority Data

Jun. 12, 2001 (SE) ...................................... 0102073

(51) Int. Cl.
A01J 5/007    (2006.01)
A01J 5/013    (2006.01)

(52) U.S. Cl. ................. 119/14.08; 119/14.02; 119/14.14

(58) Field of Classification Search .... 119/14.01–14.03, 119/14.08, 14.14, 14.15, 14.16, 14.17
See application file for complete search history.

(56) References Cited

U.S. PATENT DOCUMENTS 4,788,648 A    11/1988 Ferretti et al.
5,743,209 A *  4/1998 Bazin et al. ................. 119/14.08

FOREIGN PATENT DOCUMENTS

| EP | 0533020 | 3/1993 |
|---|---|---|
| EP | 0 666 475 A2 | 8/1995 |
| EP | 0713641 | 5/1996 |
| WO | WO 96/03859 | 2/1996 |
| WO | WO 97/05768 | 2/1997 |
| WO | WO 99/51083 | 10/1999 |
| WO | WO 00/64242 | 11/2000 |

(Continued)

OTHER PUBLICATIONS

"Melkwinning" —handbook, Aug. 1996, pp. 213-220.

(Continued)

Primary Examiner — Son T. Nguyen
(74) Attorney, Agent, or Firm — Harness, Dickey & Pierce, P.L.C.

(57) ABSTRACT

In a milking facility (1) provided with on-site measuring equipment (9) capable of measuring a quality and/or quantity of milk produced, wherein the milk produced is stored in a milk tank (5) and is then collected (79) by a dairy plant, there is provided a method comprising the steps of: (i) receiving (61) a measured value indicative of the quality and/or quantity of milk produced in the milking facility from the on-site measuring equipment; (ii) receiving (99) from the dairy plant a corresponding measured value indicative of the quality and/or quantity of milk collected and transported, wherein the dairy plant is provided with high-quality measuring equipment (41); (iii) comparing (93) the measured values from the on-site measuring equipment of the milking facility and from the dairy plant; and (iv) calibrating or verifying (95) the on-site measuring equipment of the milking facility depending on the result of the comparison.

10 Claims, 2 Drawing Sheets

FOREIGN PATENT DOCUMENTS

WO      WO 01/74150      10/2001

OTHER PUBLICATIONS

Leaflet "Zuivelnet-vandaag melf leveren, morgen al gegevens beschikbaar," 2000.

"Deutsche Milchwirtschaft," 1992, pp. 1473-1474.
"Deutsche Milchwirtschaft," 1996, pp. 854-855.
Decision Board of Appeal T650/04-3.2.04 dated Feb. 23, 2006.
European Notice of Opposition dated Jul. 16, 2007.

* cited by examiner

MILK MEASUREMENT AND MILK COLLECTION

TECHNICAL FIELD OF THE INVENTION

The present invention generally relates to dairy farming and dairy industry.

Particularly, the invention relates to a method and a device, respectively, in a computer-controlled milking facility aiming at improving milk measurements as performed at the milking facility, to a method and a device, respectively, in a dairy plant aiming at improving collection of milk from the milking facility as performed by the dairy plant, and to computer program products loadable into computers of the milking facility and the dairy plant, respectively, for performing the respective methods.

DESCRIPTION OF RELATED ART AND BACKGROUND OF THE INVENTION

In modern dairy farm industry there are continuous research and development activities in order to improve the efficiency of various activities such as machine milking, which, inter alia, involves increased milk yield and reduced milking time.

A major trend in this respect is an increased degree of automation of the various activities. For instance, machine milking may be performed by milking robots in a completely automated manner. Such an automatic milking system may take care of milking, feeding, milk sampling, animal traffic, etcetera in a large area wherein the dairy animals are walking about freely and are visiting the milking machine on a voluntary basis.

In order to manage a herd of dairy animals, including selection of milking animals and of breeding animals, feeding, detection of illnesses, etcetera, it is important to monitor the quantity and quality of milk produced at a milking facility on an average level, on a cow-individual basis and even on a teat-individual basis. To this end milk samples are representatively taken from the milk produced by a herd of cows, by a single cow, or by a single teat, and are sent to a laboratory for analysis on regular time basis, e.g. once or a few times a month. The result of the analysis (e.g. contents of fat, protein, bacteria, and spores, and somatic cell count values) are typically provided some days or weeks later and appropriate actions are taken based on said results.

Further, the dairy farmer is paid for the milk produced based on such results, particularly the contents of fat and protein.

In order to render the milk production more effective the milking robots may be equipped with uncomplicated milk inspection units, e.g. conductance meters and optic sensors, for measurement of some quality parameters on-site in real time. It is foreseen that such on-site measuring equipment will become more and more sophisticated as well as more and more common in the near future.

However, such milk measuring equipment nevertheless has to be of low cost such that the milk producers will invest in such equipment. One drawback of such approach, however, is that such on-site measuring equipment may not provide accurate, precise and reliable measurements, and thus, such measurements may not be valuable to the milk producer.

SUMMARY OF THE INVENTION

It is an object of the present invention to provide a method and a device, respectively, in a computer-controlled milking facility provided with on-site measuring equipment capable of measuring a quality and/or quantity of milk being produced in said milking facility, wherein the milk produced is stored in a milk tank of the milking facility and is then collected and transported to a dairy plant, which method and device improve the accuracy and reliability of the on-site measuring equipment.

It is a further object to provide such method and device, which are reliable, of low cost, and easy to implement in an existing computer-controlled milking facility.

It is still a further object to provide a computer program product loadable into a computer of the milking facility for performing the above said method when said program product is run on said computer.

It is yet a further object of the present invention to provide a method and a device, respectively, in a dairy plant, which uses a milk-collecting vehicle for collecting milk from a plurality of computer-controlled milking facilities, each provided with milk measuring equipment, e.g. a flow meter, which method and device are capable of planning an optimal milk collection route.

It is still a further object to provide such method and device, which are reliable, of low cost, and easy to implement in an existing dairy plant.

It is yet a further object to provide a computer program product loadable into a computer of the dairy plant for performing the above said method capable of planning an optimal milk collection route when said program product is run on said computer.

These objects, among others, are according to the present invention attained by methods, devices, and computer program products as claimed in the appended patent claims.

By the provision of a calibration/verification operation at the milking facility based on measurements performed by the dairy plant, or a laboratory contracted by it, the dairy plant will have an increased confidence in measurements performed by the milking facility. In some circumstances, the dairy plant needs thus only to perform random inspections of the measurements performed by the milking facility and in other circumstances the dairy plant can fully rely on the milking facility measurements.

By the communication of milk quantity measurement data to the dairy plant prior to milk collection an optimal milk collection route can be scheduled by the dairy plant. When the confidence in such milk quantity measurement data is increased, such planning is of particular interest.

If milk quality measurement data is communicated to the dairy plant prior to milk collection a milk quality-selective milk collection route can be scheduled by the dairy plant, i.e. milk of particular quality can be scheduled to be collected separately to thereby provide for delivery of milk of a quality.

Further, a scheduled time for milk collection can be communicated to the milking facility to facilitate planning of operations that may affect, or be affected by, the collection of milk at the milking facility such as e.g. cleaning of a milk tank wherein milk is stored before collection by the dairy plant.

Further characteristics of the invention and advantages thereof will be evident from the following detailed description of embodiments of the invention given hereinbelow and the accompanying FIGS. 1-2, which are given by way of illustration only, and thus are not limitative of the present invention.

In the following detailed description the milk producing animals are cows. However, the invention is not limited to cows, but is applicable to any animals having the capability to produce large quantities of milk, such as sheep, goats, buffaloes, horses, etc.

DETAILED DESCRIPTION OF EMBODIMENTS

In the following description, for purposes of explanation and not limitation, specific details are set forth, such as particular techniques and applications in order to provide a thorough understanding of the present invention. However, it will be apparent to one skilled in the art that the present invention may be practiced in other embodiments that depart from these specific details.

Figure 1:
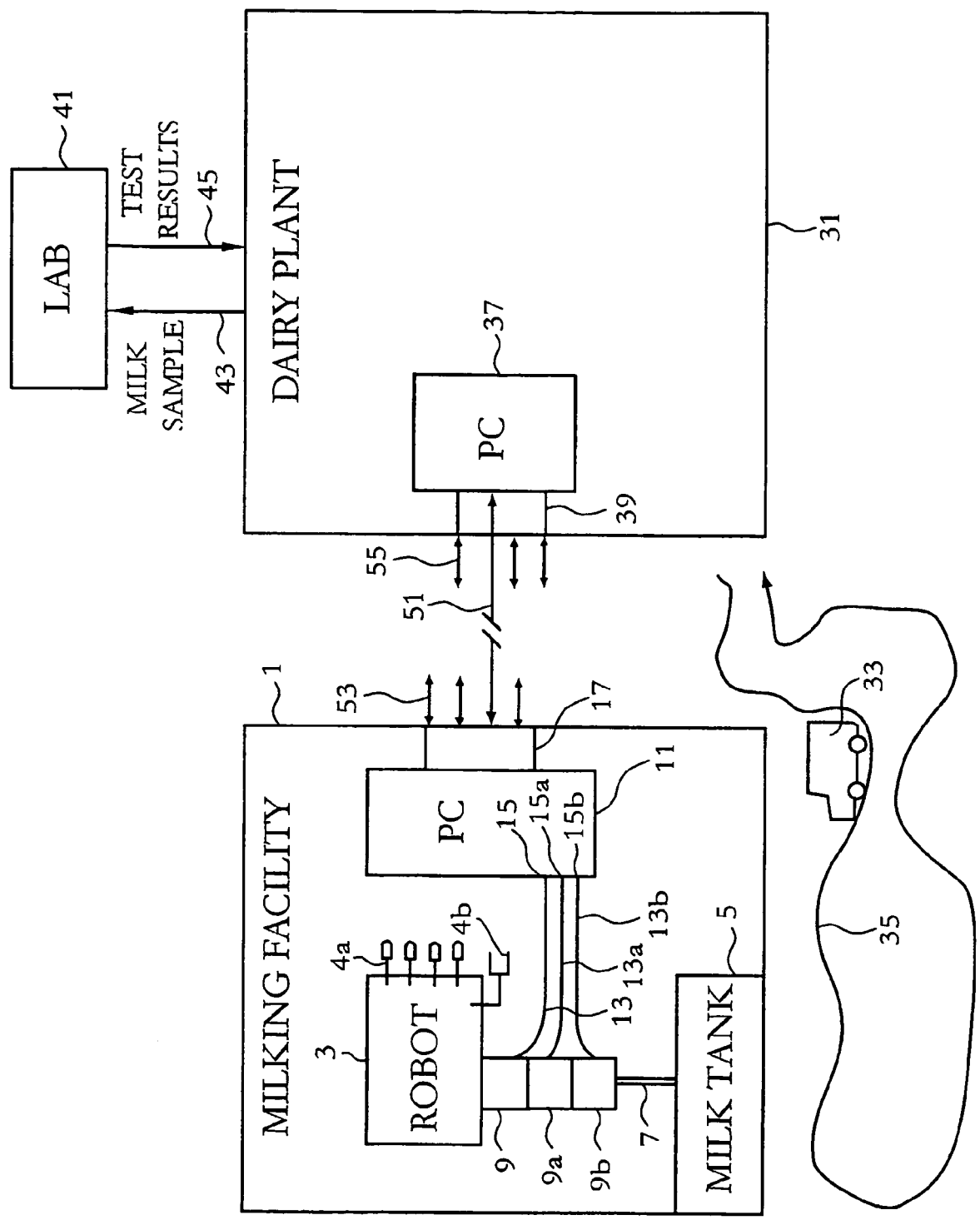
FIG. 1 illustrates, in a schematic view, a milking facility and a dairy plant, respectively, which are connected by a bi-directional communication line to provide for the present invention.

With reference to FIG. 1, which illustrates in a schematic view an automatic milking facility 1 and a dairy plant 31, respectively, which are connected by means of a bi-directional communication line 51, the present invention will be described.

The automatic milking facility 1 comprises an automatic milking robot 3 arranged for voluntary milking of freely walking cows, i.e. the cows enter the milking facility in order to be milked when they need to (or want to). The milking robot 3 includes four teat cups, schematically indicated at 4a, each being individually connectable to a source of vacuum, and each being connected to an end unit for collection of milk (not illustrated). Further, the milking facility is provided with a milk flow-measuring device capable of, during milking, in-situ measuring the individual milk flow from each teat of the cow being milked. Prior to milking, the teat cups are typically applied to the teats of the cow in some sequential order by means of a robot arm 4b.

Furthermore, there is provided a central processing unit, typically in form of a computer 11 for controlling the access to the milking robot 3 and the milking performed by the milking robot 3. The computer 11 is further holding a database of the freely walking cows and provided with an identification system for identifying a cow approaching the milking robot 3 to thereby control and manage the milking on a cow-individual, or even teat-individual, level.

The milk collected in the end unit is measured by means of a mass flow milk meter 9, after which the milk is pumped via a milk line 7 to a milk tank 5, where the milk is stored until the tank 5 is emptied by a milk collecting vehicle 33 from the dairy plant 31. Such milk collection is typically performed once a day, or every second or third day.

The measured mass flow of milk is transmitted over a signal conduit 13 to an input terminal 15 of the computer 11, such that the computer 11 can deduce information of the amount of milk stored in the milk tank 5 at every given time.

Further, the milking facility can according to the present invention be provided with further on-site measurement equipment for measuring of the quality of milk produced by the milking facility 1, such as a conductance measuring device 9a connected to a second input terminal 15a of the computer 11 via a second signal conduit 13a and/or a infrared spectrometer device 9b connected to a third input terminal 15b of the computer 11 via a third signal conduit 13b.

By means of such milk quality measurement equipment for instance the content of fat, protein, bacteria and spores, and a somatic cell count value can be obtained in the computer 11.

The milk quality measurement equipment 9a, 9b can be arranged at any location of the milk facility 1, e.g. at the milk tank 5 for measuring the quality of milk as collected from many cows, at the end unit or at the milk line 7 for measuring the quality of milk as collected from each single cow separately, or even before the end unit in the teat cups 4a or in the milk lines connecting the teat cups 4a to the end unit for measuring the quality of milk as collected from each single teat of each cow separately.

All measured values indicative of the quantity and quality of milk produced in the milking facility are stored in the computer 11.

Turning now to the dairy plant 31, which is collecting the milk from the milk tank 5 of the milking facility 1 and refines the milk collected and manufactures various products based on milk such as e.g. milk of different fat contents, yogurt, soured milk, butter, and cheese. To this end the dairy plant can include numerous machines, apparatus, equipment known in the art.

For the purpose of the present invention the dairy plant 31 is at least provided with a processing device such as a computer 37, and milk measuring and analyzing capability. Further, a milk-collecting vehicle 33 is used for delivering raw milk to the dairy plant.

The quantitative measurements of milk collected from a milking facility is typically performed by means of a calibrated and approved milk meter (not illustrated) at the milk collecting vehicle 33 while pumping the milk from the milk tank of the milking facility to the milk collecting vehicle 33. In connection thereto, a milk sample is representatively taken and transported (schematically illustrated by arrows 35 and 43) to an analyzing laboratory at the dairy plant or to a separate laboratory 41 contracted by the dairy plant 31. After an amount of time, typically 1-4 days, test results are sent to the dairy plant (schematically illustrated by arrow 45), where these results typically relate to the fat and protein contents and the somatic cell count value of the milk collected.

The payment to the milk producer is then based on the quantity and on the quality of the milk collected as measured by the dairy plant or by the contracted laboratory.

It shall be appreciated that while the milk meter and laboratory equipment used by the dairy plant 31 is high-quality equipment using well-known measuring methods and procedures, the milk measuring equipment at the milking facility is more of an uncomplicated field equipment of low cost, which may use a principle of measurement not always providing reliable results, but which yields results quickly. This holds particularly for the milk quality measuring equipment.

Thus, it is convenient to refer to the equipment used by the dairy plant as high-quality equipment, whether the field equipment used at the milking facility is referred to as on-site measurement equipment.

The present invention is concerned with communication between the milking facility 1 and the dairy plant 31 and operations, which may be performed as a result of such communication. To this end the computers 11 and 37 of the respective structures 1 and 31 are provided with a respective transceiver 17 and 39, such that a bi-directional communication line 51 can be established between the computers 11 and 37.

The transceivers 17, 39 and the communication line 51 can be of any kind, e.g. modems communicating over a called line, a fixed line, or a cellular network.

It shall further be appreciated that the dairy plant 31 can establish such communication lines to a plurality of different milking facilities or milk production plants, as well as that the milking facility 1 can establish communication lines to a plurality of different dairy plants, schematically indicated by bi-directional arrows at 53.

Communication from the milking facility 1 to the dairy plant 31 may include information as to the amount of milk stored in the milk tank 5 ready to be collected and such information may be used at the dairy plant site to plan a milk collection route, such that an effective milk collection can be realized.

The amount of milk stored in the milk tank 5 as measured on-site, and possibly the quality thereof, may be communicated to a plurality of dairy plants or may be communicated to a spot market site, e.g. on the Internet, to thereby have the milk sold to and collected by a dairy customer.

Communication from the dairy plant 31 to the milking facility 1 may include information as to the amount and quality of milk collected from the milk tank 5 and such information may be used at the milking facility site to verify or calibrate its on-site milk measuring equipment.

Figure 2:
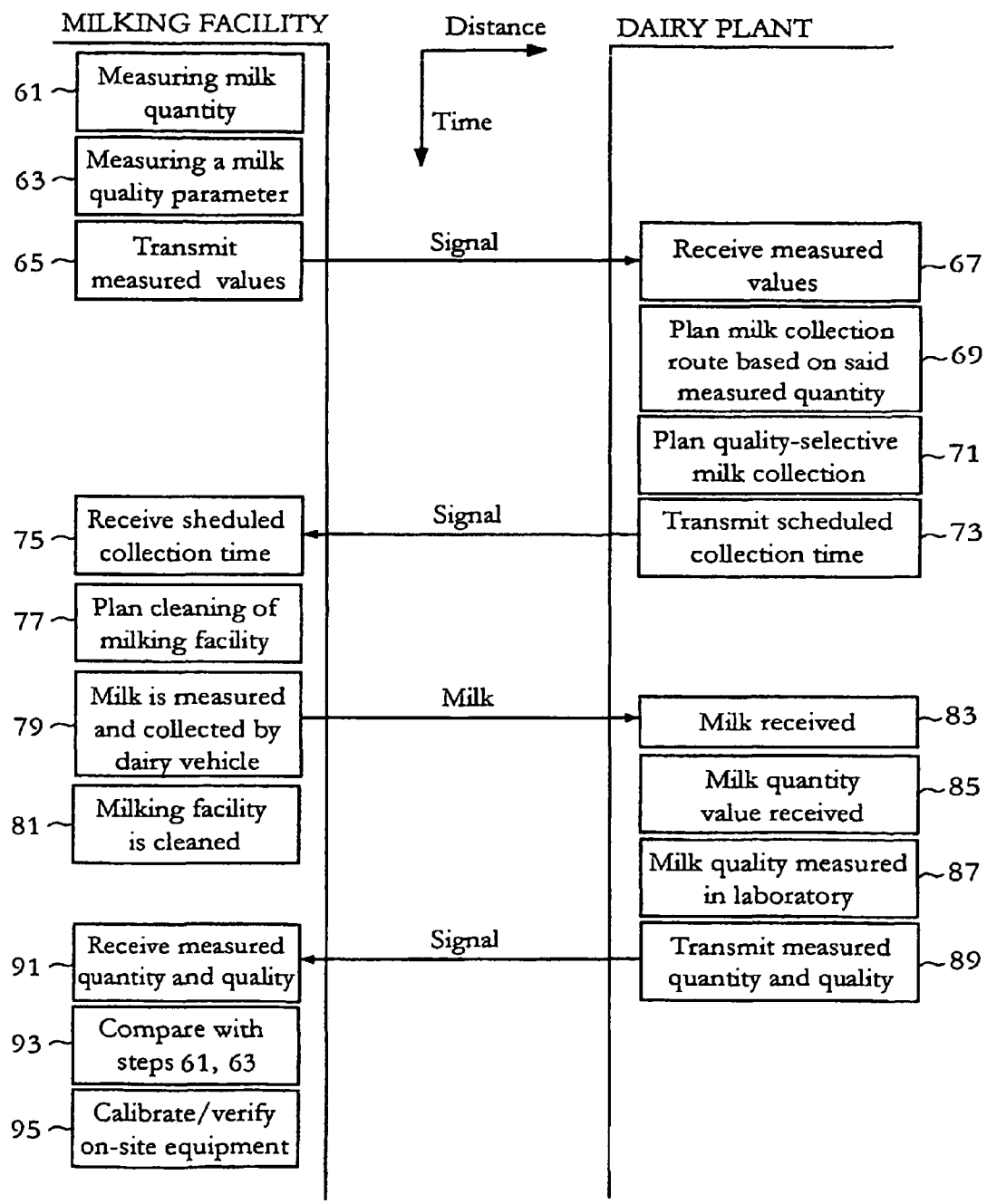
FIG. 2 illustrates, schematically, in a combined flow diagram and signaling scheme a method according to an embodiment of the present invention.

With reference next to FIG. 2 communication and operation according to a particular embodiment of the present invention will be described, where the communication is performed by means of the arrangement as illustrated in FIG. 1.

In a step 61, a milk quantity as produced in the milking facility 1 (and that can be collected) is measured by means of the on-site milk meter 9, and in a following step 63, at least one quality related parameter of the milk produced is measured by means of the measuring equipment 9*a-b*.

Next, in a step 65, these measured quantity and quality parameters are communicated to the dairy plant 31 over the communication line 51, possibly together with an identification of the milking facility 1 and a time stamp indicating the time of signaling or the time, at which the milk measurements were performed, and, in a step 67, this data is received at the dairy plant 31.

This information can be very important to the dairy plant, particularly if it has confidence in the data transmitted, and knows that the data is correct. Thus, in a step 69, a milk collection route for collection of milk is planned by the dairy plant based on the received value of milk quantity. Such planning is particularly useful if a large number of milking facilities communicate their respective milk quantities to the dairy plant 31. The planning can for instance be performed to minimize the distance that a vehicle has to move in order to collect the milk at all milking facilities. Further, if a planned route results in that the vehicle has an additional capacity of e.g. 300 liters such amount may be collected from a milking facility on, or close to, the route, which has 300 liters to be collected but which does not necessarily have a full milk tank.

It shall be noted that because the milking facilities are computer-controlled and use a voluntary milking where milking may be performed more or less continuously, there are no natural collection times, i.e. times when no milking takes place, and thus the milk can be collected at points of time convenient for the dairy plants, i.e. based on the above-said milk collection routes.

Another possibility, which may be utilized, is the knowledge of the milk quality of the milk at the different milking facilities. It is foreseen that it can be very useful to collect milk of a particular quality one day and milk of another quality the following day and to refine the milk in a manner, which is depending on the quality thereof. Thus, in a step 71 a milk collection route for quality selective collection of milk is planned by the dairy plant based on the received values of milk quantity and quality parameters.

When a milk collection route for collection of milk at the milking facility is planned a scheduled collection time for the collection of the milk is estimated, and this estimated time is, in a step 73, communicated to the milking facility 1, and then the milking facility can, in a step 77, plan operation of an activity, which affects or is affected by the milk collection.

Examples of such milk collection affected activities include various kinds of activities which need the shutdown of parts of the milking facility and thus such activities are planned to be performed while the milk is collected (when the milking facility is shutdown anyway). Cleaning of the milking facility (particularly of the milking robot 3 and the milk line 7), and maintenance of the milking facility including calibration of milk flow meters and mechanical adjustments thereof, change of milk filters, and change of teat cup liners and milk hoses are some typical milk collection affected activities.

Next, in a step, 79, the milk at the milking facility is measured and collected by the milk-collecting vehicle 33, and a milk sample is representatively taken from the milk before or during collection. Then, in a step 81, the empty milk tank 5 of the milking facility 1 is preferably cleaned, possibly along with the rest of the facility.

The collected milk is transported to the dairy plant 31, where the milk is received in a step 83, and the value of the amount of milk measured in the step 79 is forwarded to the dairy plant computer 37 in a step 85.

The milk sample is forwarded to an analyzing high-quality laboratory in a step, where, in a step 87, a quality, e.g. content of fat, protein, bacteria and/or spores, and/or a somatic cell count value are/is measured. At least one of the quality parameters measured in the step 63 is also measured in the step 87.

Values of the measured amount of milk collected as well as values of measured milk quality parameters are, in a step 89, forwarded to the milking facility.

Alternatively, the dairy plant is itself provided with analyzing high-quality equipment for measuring a quality, e.g. content of fat, protein, bacteria and/or spores, and/or a somatic cell count value.

Still alternatively, values of measured milk quality parameters are forwarded directly to the milking facility from the laboratory.

At the milking facility these values, received in a step 91, are treated as true ones (due to the more advanced measuring equipment at the dairy plant), and thus, in a step 93 these values are compared with the earlier measured values at the milking facility (measured in steps 61 and 63 by the on-site measurement equipment 9, 9*a*, 9*b*), and finally, in a step 95 the on-site measurement equipment 9, 9*a*, 9*b* is calibrated or verified depending on the result of the comparison performed in the step 93.

Such calibration may be performed in a plurality of ways and is typically performed based on some average value such that systematical errors of the milk meter 9, 9*a*, 9*b* are eliminated and the accuracy of subsequent performed measurements is improved.

It shall further be appreciated that as an alternative to the milk meter 9, or a complement thereto, a milk level indicator may be provided at the milk tank 5 for sensing the level of milk therein.

It shall be appreciated that both the milking facility and the dairy plant can benefit from such a co-operation, i.e. communication and exchanging of information. Particularly, operations performed in steps 69 and 71 at the dairy plant and operations performed in steps 77 and 95 at the milking facility are based on two-way communication between the parties.

The milking facility can verify its on-site measuring equipment and the dairy plant can—in the view of having confidence in the on-site measuring equipment of the milking facility thanks to the verification (and calibration thereof)—plan its milk collection routes, and even plan and perform milk collection routes for quality-selective milk collection.

It will be obvious that the invention may be varied in a plurality of ways. Such variations are not to be regarded as a departure from the scope of the invention. All such modifications as would be obvious to one skilled in the art are intended to be included within the scope of the appended claims.

The invention claimed is:

1. A method in a computer-controlled milking facility provided with on-site measuring equipment capable of measuring a quality and/or quantity of milk being produced in said milking facility, wherein the milk produced is stored in a milk tank of the milking facility and is then collected and transported to a dairy plant, said method comprising the steps of:
   providing a first measured value of milk produced in the milking facility as measured by the on-site measuring equipment of the milking facility;
   receiving a corresponding second measured value of said milk from a site equipped with high-quality measuring equipment, and to which a sample of said milk is transported, or from the dairy plant to which said milk is transported, wherein the dairy plant is provided with high-quality measuring equipment, or is in communication with the site equipped with high-quality measuring equipment, and to which a sample of said milk is transported, the first measured value and the second measured value measuring at least one same characteristic of the milk;
   comparing the at least one same characteristic of the first and the second measured values; and
   calibrating said on-site measuring equipment of the milking facility depending on the result of said comparison.

2. The method as claimed in claim 1 wherein said first and second measured values are indicative of the quantity of collected and transported milk, and said first measured value is measured by a milk flow meter, a group of milk flow meters, or a milk level indicator at the milk tank.

3. The method as claimed in claim 2 wherein said corresponding second measured value is received from a dairy plant as measured by high-quality equipment located at the dairy plant or at a vehicle used for the collection of the milk.

4. The method as claimed in claim 2 wherein said first measured value is communicated to said dairy plant prior to the collection of the milk to thereby allow for planning of a milk collection route and time schedule by the dairy plant.

5. The method as claimed in claim 4 wherein an indication of a time when the milk is to be collected is received from said dairy plant prior to the collection of the milk to thereby provide for planning of a milk collection related operation.

6. The method as claimed in claim 2 wherein the first measured value is communicated to a plurality of dairy plants or is communicated to a market site prior to the collection of the milk.

7. The method as claimed in claim 2 wherein
   a further measured value indicative of the quality of milk produced in the milking facility as measured by the on-site measuring equipment of the milking facility is provided;
   a further corresponding measured value indicative of the quality of milk transported to the dairy plant as measured by the high-quality measuring equipment is received;
   said further measured values indicative of the quality of milk from the measuring equipment of the milking facility are compared with said corresponding measured value from the high-quality measuring equipment; and
   said measuring equipment of the milking facility is calibrated or verified depending on the result of said comparison of further measured values indicative of the quality of milk.

8. The method as claimed in claim 1 wherein said first and second measured values are indicative of the quality of said milk.

9. The method as claimed in claim 8 wherein said first and second measured values indicative of the quality of milk transported to the dairy plant are measures of the content of any of fat, protein, bacteria or spores, or is a somatic cell count value.

10. The method as claimed in claim 8 wherein said first measured value indicative of the quality of milk is communicated to said dairy plant prior to the collection of the milk to thereby allow for planning of quality selective milk collection routes by the dairy plant.

* * * * *

UNITED STATES PATENT AND TRADEMARK OFFICE
CERTIFICATE OF CORRECTION

| | | |
|---|---|---|
| PATENT NO. | : 7,997,228 B2 | Page 1 of 1 |
| APPLICATION NO. | : 10/480435 | |
| DATED | : August 16, 2011 | |
| INVENTOR(S) | : Jan Eriksson | |

It is certified that error appears in the above-identified patent and that said Letters Patent is hereby corrected as shown below:

Title Page, Item (30) should read:

--(30) Foreign Application Priority Data

June 12, 2001   (SE) ...........................0102073-4--.

Signed and Sealed this
Twenty-fifth Day of October, 2011

David J. Kappos
*Director of the United States Patent and Trademark Office*